US005232573A

United States Patent [19]
Rosenvold

[11] Patent Number: 5,232,573
[45] Date of Patent: Aug. 3, 1993

[54] INTEGRAL ELECTROPHORESIS GEL FORM

[76] Inventor: Eric Rosenvold, 9 Meadowview Rd., Topsfield, Mass. 01983

[21] Appl. No.: 961,480

[22] Filed: Oct. 15, 1992

[51] Int. Cl.[5] .................. G01N 27/26; G01N 27/447; B01D 57/02
[52] U.S. Cl. ............................ 204/299 R; 204/182.8; 204/180.1
[58] Field of Search ............ 204/299 R, 182.8, 180.1, 204/182.9

[56] References Cited

U.S. PATENT DOCUMENTS

| | | | |
|---|---|---|---|
| 4,246,222 | 1/1981 | Monthony | 204/182.8 X |
| 4,339,327 | 7/1982 | Tyler | 204/299 R |
| 4,883,577 | 11/1989 | Sugimoto et al. | 204/299 R |
| 5,149,417 | 9/1992 | Foley et al. | 204/299 R |
| 5,164,065 | 11/1992 | Bettencourt et al. | 204/299 R |
| 5,186,807 | 2/1993 | Sanford et al. | 204/299 R |
| 5,188,790 | 2/1993 | Magnant | 204/299 R X |
| 5,188,963 | 2/1993 | Stapleton | 204/299 R |

Primary Examiner—John Niebling
Assistant Examiner—John S. Starsiak, Jr.
Attorney, Agent, or Firm—Iandiorio & Dingman

[57] ABSTRACT

An integral electrophoresis gel form for placement between front and back gel plates including a pair of spaced side strips for placement between the side edges of the plates to seal the edges, and a transverse strip connected to at least one of the side strips for placement between the top ends of the plates to seal the ends. The transverse strip is separable from the side strips to allow the introduction of samples between the plates toward their top ends after removal of the transverse strip.

25 Claims, 3 Drawing Sheets

INTEGRAL ELECTROPHORESIS GEL FORM

FIELD OF INVENTION

This invention relates to an integral form for sealing the top and side edges of electrophoresis gel plates and also to establish a distinct, straight top gel line.

BACKGROUND OF INVENTION

DNA sequencing techniques require denaturing polyacrylamide gels. The gels are typically formed between two closely spaced flat glass plates. The bottom and edges of the plates are sealed as best they can be and the gel is then poured into or injected in the space between the plates. The gel then polymerizes in situ.

Standard techniques for preparing the plates are described in *Molecular Cloning—A Laboratory Manual*, Sambrook et al., Cold Spring Harbor Laboratory Press (second edition 1989), and *Current Protocols in Molecular Biology*, Ausubel et al., Greene Publishing Associates and Wyle-Interscience, New York, N.Y., 1991, supplement 16, unit 7.6 (Stalko, B.). The techniques describe processes in which two spacer strips are placed along the sides of the bottom plate, and in some instances a lower spacer is placed along the bottom edge of the lower plate. The top plate is then carefully placed on top of the lower plate. The corners where the spacers meet are then typically sealed with agarose or vacuum grease. After the top plate is placed on the bottom plate the edges are bound with one or more layers of electrical tape in an attempt to make a water tight seal and binder clips are placed on the sides and bottom.

These procedures, however, suffer from a number of drawbacks that make them difficult at best. First, a lot of technician's time is spent in aligning the two or three spacers between the glass plates, and attempting to seal the joints between the spacers with grease or applying tape without wrinkles to the sides and bottoms of the plates so as to make a tight seal. Even after all this time and care, the gel solution frequently leaks out from the bottom corners even for experienced technicians. Since the solution is expensive, messy and neurotoxic, extra time and care is then required in clean up.

Additionally, these techniques require that the flat side of a shark's tooth comb, or a comb with preformed wells, be inserted between the plates at the top edge after the gel solution is poured but before it polymerizes in order to form a flat surface at the top of the gel or to form sample introduction wells n the gel, respectively. This step also requires operator expertise. Great care must be taken that the comb is inserted far enough, but not too far and that bubbles of air are not trapped between the comb and the gel. Furthermore, inserting the comb causes some of the solution to spill out the top of the plates, adding to the clean up effort.

After the gel polymerizes, the extraneous polyacrylamide must be removed from around the combs. If a bottom spacer is used, it must be removed, resulting in an air space between the plates at the bottom of the gel. Since there must be a conductive path through the gel into the buffer solution in which the plates are placed, when the plates are lowered into the buffer solution this air space must be carefully filled with buffer. This is usually accomplished by squirting buffer between the plates using a syringe with a bent needle, which takes additional time and expertise. In addition, if all of the air bubble is not carefully removed, a portion of the gel will not be properly subjected to the electrophoresis voltage, thereby ruining a portion of the results, creating additional waste and cost.

SUMMARY OF INVENTION

It is therefore an object of this invention to provide a electrophoresis gel form that greatly simplifies the gel casting process.

It is a further object of this invention to provide such a form that is easy to lay up.

It is a further object of this invention to provide such a form that inhibits leakage at the plate corners.

It is a further object of this invention to provide such a form which requires little expertise to use.

It is a further object of this invention to provide such a form which creates a sharp flat surface at the top of the gel perpendicular to the edges of the plates without any operator expertise.

It is a further object of this invention to provide such a form that automatically provides for proper sample-introduction wells.

It is a further object of this invention to provide such a form which automatically creates a gel top flat surface that is at the right location to accept a shark's tooth comb.

It is a further object of this invention to provide such a form which results in a gel without an air space at its bottom.

It is a further object of this invention to provide such a form which results in operation that does not require buffer to be injected between the gel-form plates after the gel is cast.

It is a further object of this invention to provide such a form which does not require the edges of the plates to be taped.

This invention results from the realization that a simple to use and extremely effective electrophoresis gel form may be accomplished with an integral body including two elongated parallel side strips interconnected by a transverse strip having a flat edge facing toward the bottom of the plate, and a shark's tooth comb along its other edge, in which the transverse strip is easily separable from the side strips so that the comb may be removed after polymerization and turned around and placed against the top of the polymerized gel to allow sample introduction.

This invention features an integral electrophoresis gel form for placement between front and back gel plates, The form includes a pair of spaced side strips for placement between the side edges of the plates to seal the edges, and a transverse strip connected to at least one of the side strips, and preferably both, for placement between the top ends of the plates to seal the ends. Further included are means for allowing separation of the transverse strip from the side strips to allow the introduction of samples between the plates toward their top ends after removal of the transverse grip. Preferably, the side strips are the same thickness and they are parallel and are substantially the lengths of the plates, with their top ends extending beyond the plates so that they may be grasped for separation of the transverse strip from the side strips. The transverse strip is preferably perpendicular to the side strips and has the same thickness of the side strips so that the form seals three sides of the cavity formed between the plates when the gel form is in place. The form may be made from a material such as a plastics material.

The transverse strip preferably includes either a plurality of teeth forming a shark's tooth comb or rectangular teeth for forming a series of sample introduction wells into the polymerized gel. For the embodiment in which the transverse strip includes a shark's tooth comb on its outside edge, the inner edge facing the other ends of the plates is preferably flat to form a flat sharp edge to the top of the gel. The transverse strip may include a transverse slot for introduction of gelling solution.

The means for allowing separation of the transverse strip preferably is accomplished with a cut extending from the interior edge of the transverse strip and into the side strips. The cut is preferably angled toward the side strips. The cuts are preferably proximate the joint between the transverse strip and the side strips, and made convergent. An alternative form of allowing the separation may be any line of form material weakening. This may be accomplished for example with a plurality of spaced slots or spaced cuts, or a score line or score lines. The line or weakening is preferably transverse to the inner edge of the transverse strip.

DISCLOSURE OF PREFERRED EMBODIMENTS

Other objects, features and advantages will occur to those skilled in the art from the following description of a preferred embodiment and the accompanying drawings in which.

This invention may be accomplished in an integral electrophoresis gel form for placement between front and back gel plates. The form preferably includes a pair of spaced, elongated, parallel side strips interconnected by a transverse strip at right angles to the side strips and having a flat edge facing the bottom of the plates. The gel form also includes means, such as a pair of convergent cuts extending from the transverse strips into the side strips, for allowing the transverse strip to be separated from the side strips to allow the introduction of samples onto the polymerized gel after removal of the transverse strip.

Figure 1:
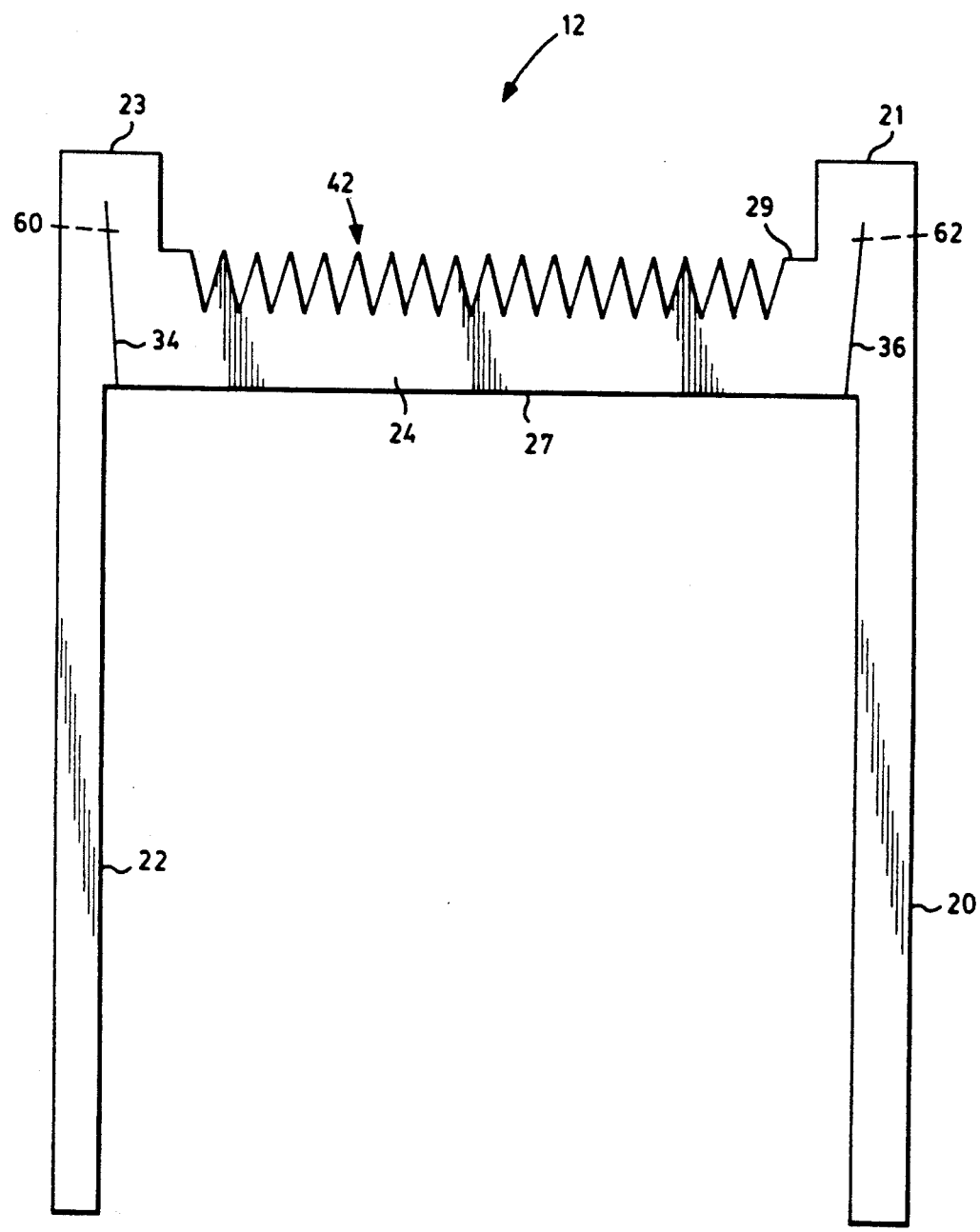
FIG. 1 is a top plan view of an integral electrophoresis gel form according to this invention.

There is shown in FIG. 1 integral electrophoresis gel form 12 according to this invention. Form 12 includes elongated parallel spaced side strips 20 and 22 interconnected by transverse perpendicular strip 24. Preferably, strip 24 is placed close to ends 23 and 21 of strips 22 and 20, respectively, as shown. Transverse strip 24 has lower edge 27 that in use forms a sharp flat top edge of the polymerized gel, as further described below. Top edge 29 in one embodiment comprises a shark tooth comb of the type known in the art so that the transverse strip can be turned around and also used as a comb for introduction of the samples onto the electrophoresis gel.

Transverse strip 24 is made separable from side strips 22 and 20, in this embodiment by including cuts 34 and 36 through the material of form 12 and by for example cutting with scissors along lines 60 and 62 (FIG. 1) after the gel has polymerized. These cuts preferably extend from edge 27 of strip 24 into strips 22 and 20, but not all the way through the side strips so that the form is a one piece, integral form that is easy to handle and also presents an uninterrupted inner boundary along three sides so that the elongated sides and top of the gel plates are fully sealed by the form. An alternative to cuts 34 and 36 would be any line of weakening of the material of form 12, for example a series of spaced-apart impressions or gaps in the material, or a score line that does not run all the way through the material. It is important only that there is created in the form a separable joint between the transverse member and the side members which is accessible when the gel form is properly clamped between the glass plates. The integral gel form design then is leak-proof, making it possible to cast a gel horizontally without using tape or grease to seal the corners.

Figure 2:
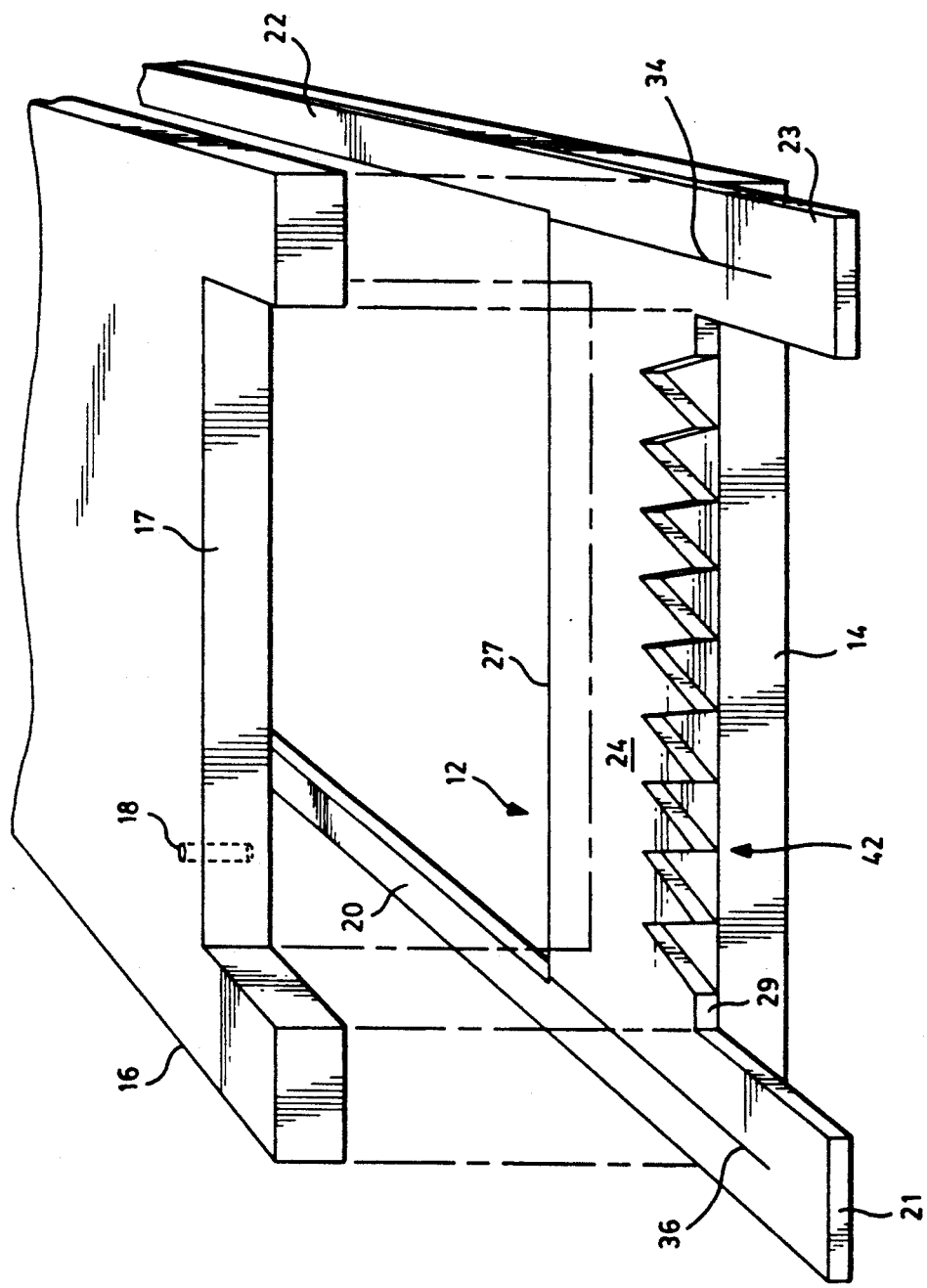
FIG. 2 is an exploded axonometric view of the gel form of FIG. 1 in place between gel plates.

Form 12 is shown in use in place between lower plate 14 and upper plate 16 in FIG. 2. In use, form 12 is placed on lower plate 14 so that the ends of strips 22 and 20 are just at the bottom edge of plate 14. Then, upper plate 16 is carefully placed over form 12 so that the top 17 of plate 16 is parallel to edge 27 of transverse strip 24, and falls somewhere below the sharks tooth comb 42 of strip 24. The sides and bottom of the assembly may be taped if desired, although all that is typically required is the placement of the standard clip along the sides. With the assembly lying flat in a horizontal plane the liquid gel solution is introduced between the plates through hole 18 in top plate 16. The liquid does not spill out of the open bottom end due to liquid surface tension. The solution is poured or injected through hole 18 until it fills the space, and then left to polymerize. Flat edge 27 of strip 24 creates a flat top edge to the gel at right angles to the gel edges and thus parallel to the bottom of the gel so that the entire gel plane is uniform (rectangular). Cuts or weakened lines 34 and 36 allow transverse member 24 to be broken away from members 20 and 22 so that member 24 can be turned around and inserted back between plates 14 and 16 so the comb can be used to facilitate the introduction of the samples to be sequenced against the top of the gel.

A preferred form of transverse member is shown in FIG. 2. Transverse member 24 includes shark's tooth comb edge 42 of the type known in the art on the outer edge of transverse strip 24 that is not exposed to the gel. Accordingly, when member 24 is separated from the side members, it can be turned over and inserted against the top of the gel to form the sample introduction wells. Thus, a separate comb is not necessary, nor is it necessary to clean the teeth of the comb as is often done with the combs used today that are subjected to leakage of the gel solution.

Figure 3:
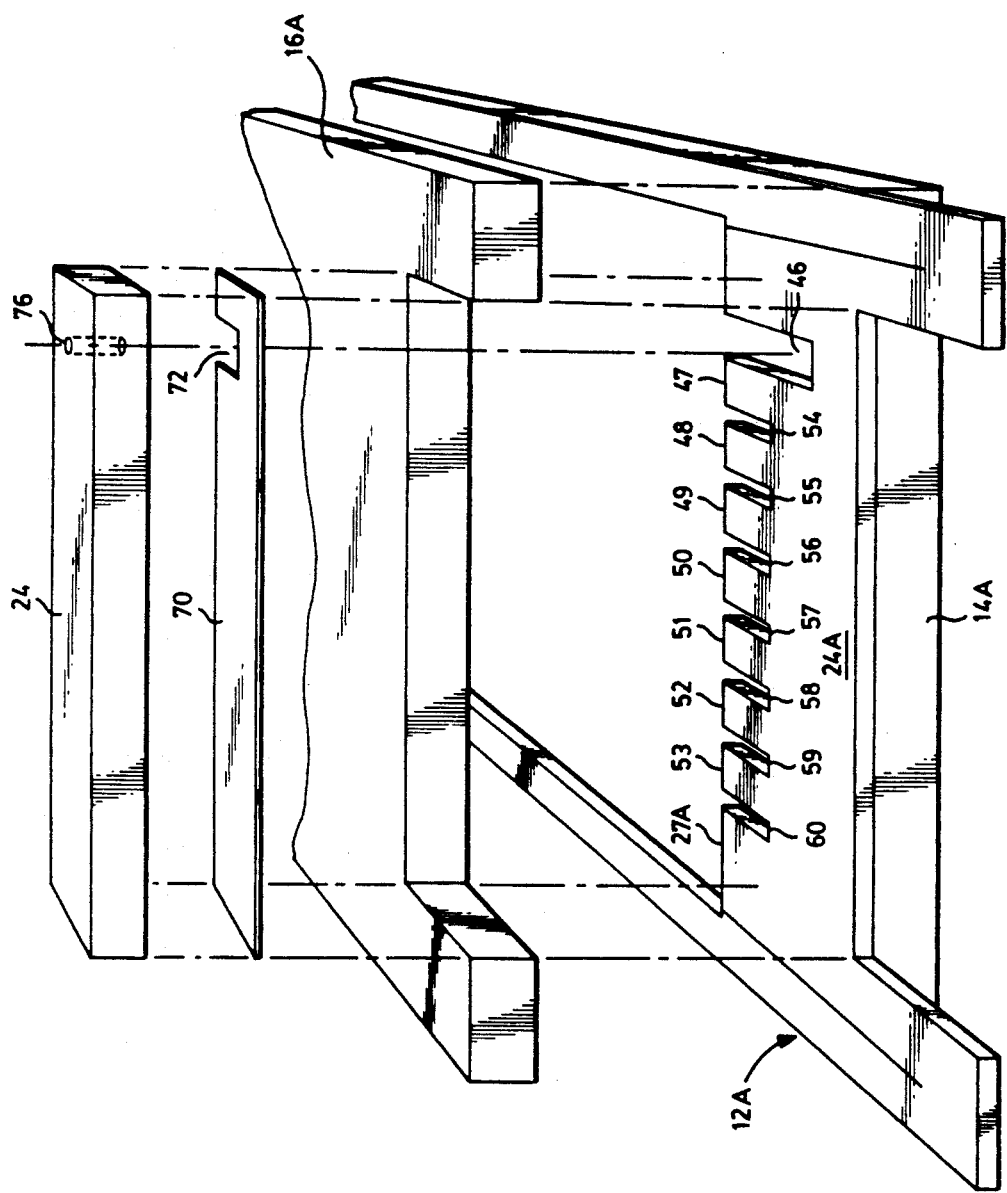
FIG. 3 is an exploded axonometric view of an alternative transverse strip and means for introducing the gelling solution between the plates.

An alternate form of the transverse strip and means for allowing introduction of the gelling solution is shown in FIG. 3. Form 12a includes transverse strip 24a having teeth 47 through 53 defining gaps 54 through 60. Also included is larger gap 46. In use, top gel plate 16a lies between lower strip edge 27a and the upper end of slot 46 so that slot 46 is partially exposed to the air. This provides a small gap into which the gel solution may be poured, for example using a small block of plexiglass 74 which has hole 76 therethrough for accepting a tube leading to a funnel into which the solution is poured. Paper piece 70 with slot 72 aligned with slot 46 may be used to effect a seal between block 74 and member 24a to inhibit solution leakage. The other end of hole 76 is lined up with gap 46 to allow an easy means of introducing the gel solution between the plates using a syringe and without spilling the solution. The solution then also fills gaps 54 through 60. After the solution polymerizes, and strip 24a is removed, the top end of the gel is left with a number of spaced ridges or teeth with gaps therebetween in the shape of elements 47 through 53 that are then used as wells for the introduction of a plurality of samples to be sequenced.

The gel form of this invention is preferably made of a substance that is inert to the gel solution, such as the plastics styrene or mylar. Styrene is currently preferred because it is recyclable. Additionally, the entire gel form is preferably of uniform thickness so that there is good sealing along the three edges of the plate. Alternatively, the side strips can have a desired thickness profile to accomplish a desired gel thickness profile.

Although specific features of the invention are shown in some drawings and not others, this is for convenience only as some feature may be combined with any or all of the other features in accordance with the invention.

Other embodiments will occur to those skilled in the art and are within the following claims.

What is claimed is:

1. An integral electrophoresis gel form for placement between front and back gel plates, comprising:
   a pair of spaced side strips for placement between the side edges of the plates to seal the edges;
   a transverse strip connected to at least one of said side strips for placement between the top ends of the plates to seal the ends; and
   means for allowing separation of said transverse strip from said side strip to allow the introduction of samples between the plates toward their top ends after removal of said transverse strip.

2. The integral electrophoresis gel form of claim 1 in which said side strips are of the same thickness.

3. The integral electrophoresis gel form of claim 1 in which said side strips are parallel.

4. The integral electrophoresis gel form of claim 1 in which said side strips are substantially the length of the plates.

5. The integral electrophoresis gel form of claim 1 in which said transverse strip is perpendicular to said side strips.

6. The integral electrophoresis gel form of claim 1 in which said transverse strip is the same thickness as said side strips.

7. The integral electrophoresis gel form of claim 1 in which said transverse strip includes a plurality of teeth.

8. The integral electrophoresis gel form of claim 7 in which said teeth extend beyond the end of a plate.

9. The integral electrophoresis gel form of claim 7 in which said teeth are angled.

10. The integral electrophoresis gel form of claim 7 in which said teeth are rectangular.

11. The integral electrophoresis gel form of claim 1 in which said transverse strip includes a flat edge facing the other ends of the plates.

12. The integral electrophoresis gel form of claim 1 in which said transverse strip is connected between both said side strips.

13. The integral electrophoresis gel form of claim 1 in which said transverse strip includes a transverse slot for introduction of gelling solution.

14. The integral electrophoresis gel form of claim 1 in which said means for allowing separation includes a cut extending from the interior edge of said transverse strip.

15. The integral electrophoresis gel form of claim 14 in which said cut extends into a said side strip.

16. The integral electrophoresis gel form of claim 14 in which said cut is angled toward a said side strip.

17. The integral electrophoresis gel form of claim 14 in which said means for allowing separation includes two cuts, each one proximate a joint between said transverse strip and said side strips.

18. The integral electrophoresis gel form of claim 17 in which said two cuts are convergent.

19. The integral electrophoresis gel form of claim 1 in which said means for allowing separation includes a line of form material weakening.

20. The integral electrophoresis gel form of claim 19 in which said line is transverse to the inner edge of said transverse strip.

21. The integral electrophoresis gel form of claim 19 in which said line includes a plurality of spaces slots.

22. The integral electrophoresis gel form of claim 19 in which said line includes a plurality of spaced cuts.

23. The integral electrophoresis gel form of claim 1 in which said side and transverse strips are made of plastic.

24. An integral electrophoresis gel form for placement between front and back gel plates, comprising:
   a pair of spaced, parallel side strips for placement along the edges between the plates to seal the edges;
   a transverse strip connected perpendicularly between said side strips proximate adjacent ends of said side strips; and
   a pair of cuts extending from the inner side of said transverse strip for allowing separation of said transverse strip from said side strips.

25. The integral electrophoresis gel form of claim 24 in which said cuts extend into said side strips.

* * * * *